US007935043B2

(12) United States Patent
Fender

(10) Patent No.: US 7,935,043 B2
(45) Date of Patent: May 3, 2011

(54) METHODS AND APPARATUS FOR CONTROLLED ADDITION OF SOLUTIONS TO BLOOD COMPONENTS

(75) Inventor: Logan Fender, Lakewood, CO (US)

(73) Assignee: CaridianBCT, Inc., Lakewood, CO (US)

( * ) Notice: Subject to any disclaimer, the term of this patent is extended or adjusted under 35 U.S.C. 154(b) by 292 days.

(21) Appl. No.: 12/234,960

(22) Filed: Sep. 22, 2008

(65) Prior Publication Data

US 2009/0166298 A1 Jul. 2, 2009

Related U.S. Application Data

(60) Provisional application No. 61/016,697, filed on Dec. 26, 2007.

(51) Int. Cl.
*B04B 7/12* (2006.01)
(52) U.S. Cl. .......................................................... 494/45
(58) Field of Classification Search ...................... 494/45
See application file for complete search history.

(56) References Cited

U.S. PATENT DOCUMENTS

| 6,200,287 | B1 | 3/2001 | Keller et al. |
| 6,773,413 | B2 | 8/2004 | Keller et al. |
| 7,052,606 | B2 | 5/2006 | Gibbs et al. |
| 2003/0211927 | A1* | 11/2003 | Cantu et al. ..................... 494/45 |

OTHER PUBLICATIONS

U.S. Appl. No. 09/672,519, filed Sep. 27, 2000, Gibbs.

* cited by examiner

*Primary Examiner* — Walter D Griffin
*Assistant Examiner* — Timothy Cleveland
(74) *Attorney, Agent, or Firm* — John R. Merkling; Edna M. O'Connor; Laura B. Arciniegas

(57) ABSTRACT

A centrifugal blood processing apparatus comprising a centrifuge rotor, a separation chamber, a tubing set for conducting blood components and fluids and having an inlet line, an outlet line and a storage solution line in fluid communication with the outlet line at a junction. The apparatus controls pumps to conduct a predetermined quantity of storage solution to a collected blood component. The apparatus also purges blood components in the tubing set by applying a negative pressure and positive pressure. A disposable blood processing set has a separation chamber; a tubing set including an inlet line in fluid and an outlet and a storage solution line connected to the outlet line at a junction.

8 Claims, 9 Drawing Sheets

US 7,935,043 B2

METHODS AND APPARATUS FOR CONTROLLED ADDITION OF SOLUTIONS TO BLOOD COMPONENTS

FIELD OF INVENTION

The present invention relates generally to the field of extracorporeal blood processing methods and apparatus which are particularly useful in blood component collection, and more particularly, the present invention relates to methods and apparatus for the controlled addition of storage solutions to platelets or red blood cells, preferably collected with an aphaeresis system.

BACKGROUND OF THE INVENTION

One well-known type of extracorporeal blood processing involves an aphaeresis system and procedure in which blood is removed from a donor or a patient (hereafter cumulatively referred to as a donor), directed to a blood component separation device (e.g., centrifuge), and separated into various blood component types (e.g., red blood cells, white blood cells, platelets, plasma) for collection or therapeutic purposes. One or more or all of these blood component types may either be collected and treated for therapeutic purposes before storage or return to a patient, while the remainder may simply be returned to the donor or patient.

A number of factors may affect the commercial viability of an aphaeresis system. One factor relates to the time and expertise required of an individual to prepare and operate the aphaeresis system. For instance, reducing the time required by the operator to complete an entire collection procedure, as well as reducing the complexity of these actions, can increase productivity or lower the potential for operator error. Moreover, reducing the dependency of the system on the operator may further lead to reductions in the credentials desired/required for the operators of these systems.

Performance-related factors also affect the commercial viability of an aphaeresis system. Performance may be judged in terms of the collection efficiency of the aphaeresis system, which may impact or improve product quality and/or may in turn reduce the amount of processing time and thus decrease operator burden and increase donor convenience. The collection efficiency of a system may of course be gauged in a variety of ways, such as by the amount of a particular blood component type which is collected in relation to the quantity of this blood component type which passes through the aphaeresis system. Performance may also be evaluated based upon the effect which the aphaeresis procedure has on the various blood component types. For instance, it is desirable to minimize the adverse effects on the blood component types as a result of the aphaeresis procedure.

An apparatus and method for red blood cell filtration in conjunction with aphaeresis separation is also disclosed in the commonly-owned U.S. patent applications Ser. No. 09/672,519, filed Sep. 27, 2000, herein incorporated by reference. Further background on aphaeresis red blood cell separation and collection can be found in the PCT publication WO99/11305, which is also incorporated herein by this reference. Commonly-owned U.S. Pat. No. 7,052,606 is directed to red blood cell filtration, but also discusses the need to add storage solution to a collected blood component and certain means whereby storage solution may be added to the collected component.

SUMMARY OF THE INVENTION

The present invention generally relates to extracorporeal blood processing. Since each of the various aspects of the present invention may preferably be incorporated into an aphaeresis system (e.g., whether for blood component collection in which "healthy" cells or other blood components are removed from the donor blood for later transfusion, or for therapeutic "unhealthy" blood component removal), the present invention will be described in relation to such aphaeresis systems. Aphaeresis may often imply the return of certain blood components back to the donor. However, certain aspects of the present invention may be suited for extracorporeal blood processing applications in which all donated blood components are retained and such are also intended within the scope of the present invention.

An aphaeresis system which may be used with one or more aspects of the present invention generally includes at least a blood component separation device (a membrane-based separation device, and/or a rotatable centrifuge element, such as a rotor and channel combination), which provides the mechanism and/or the forces required to separate blood into various blood component types, such as red blood cells, white blood cells, platelets, or plasma. In one preferred embodiment, the separation device includes a centrifuge channel which receives a disposable blood processing vessel. Typically, a donor or perhaps a patient (collectively referred to hereafter as a donor) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor or patient and directed to the blood component separation device such that at least one type of blood component may be separated and removed from the blood, either for collection or for therapy. An additive/storage solution is added to the red blood cells or platelets after collection. A blood return reservoir has heretofore been used to receive selected blood components before returning those components to the donor. In the present invention, controls are provided to prime parts of a blood processing tubing and collection assembly with storage solution after the collection of selected blood components. Certain connections in the blood processing tubing and collection assembly allow storage solution to be flushed past peristaltic pumps into the return reservoir. Sensors in the return reservoir are used to confirm the presence of storage solution and to calibrate the solution within the tubing and collection assembly. A controlled volume of the additive/storage solution can then be pumped into a storage bag containing red blood cells or platelets. The volume is controlled or metered by the action of peristaltic pumps, which move a known quantity of fluid per pump revolution. The apparatus confirms the presence of storage solution in the system before pumping the storage solution into bags containing collected blood components. Self-priming with storage solution and metered delivery of solution reduces the requirements for operator intervention and possible error and improves the accuracy of blood component mixing with storage solution.

These and still further aspects of the present invention are more particularly described in the following description of the preferred embodiments presented in conjunction with the attached drawings which are described briefly below.

DETAILED DESCRIPTION

The present invention will be described in relation to the accompanying drawings. Generally, the primary aspects of the present invention relate to both procedural and structural improvements in or a sub-assembly for use with a blood processing aphaeresis system. However, certain of these improvements may be applicable to other extracorporeal blood processing applications whether any blood components are returned directly to the donor or otherwise; and such are within the scope of the present invention as well.

Figure 1:
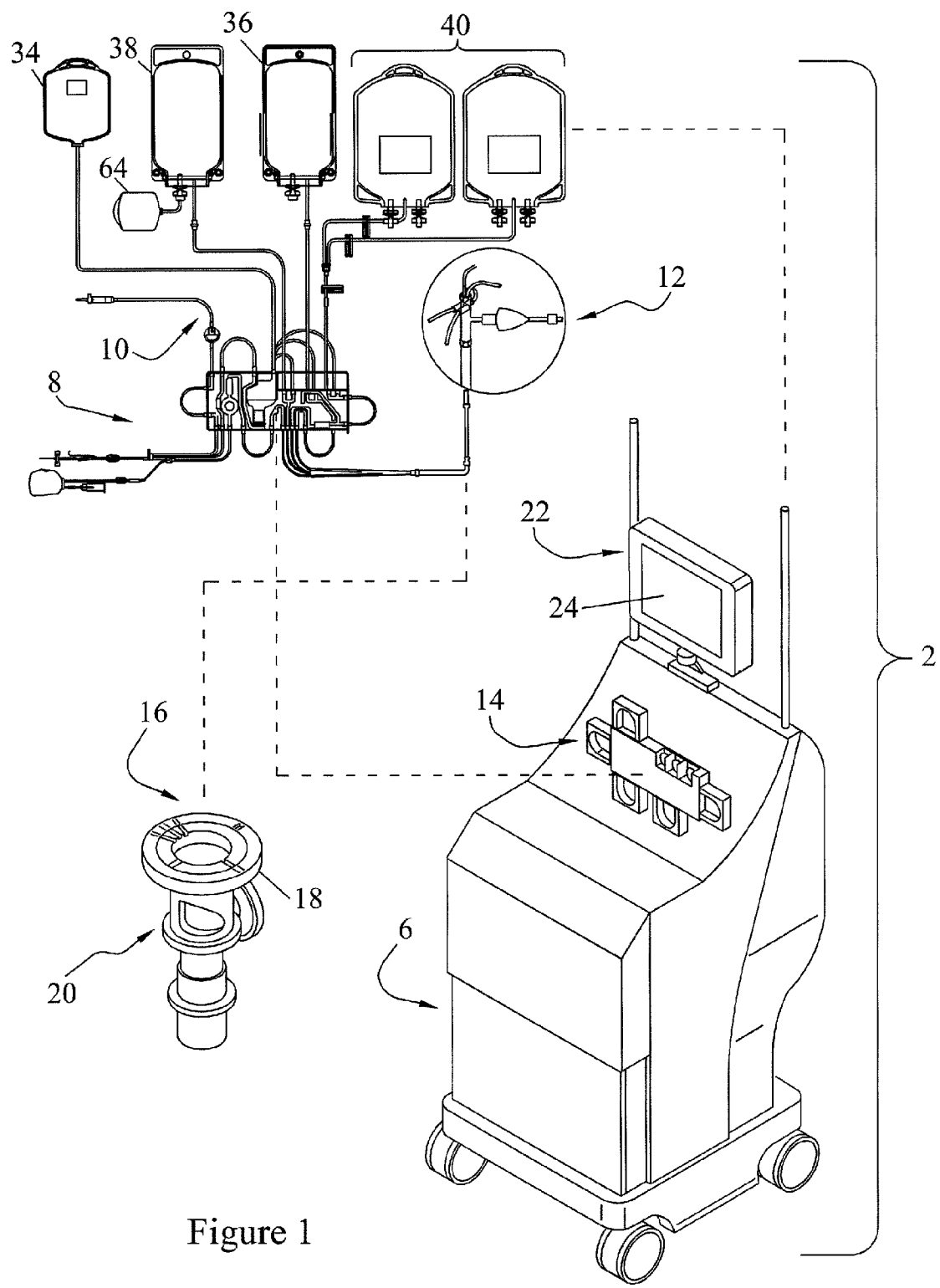
FIG. 1 is a schematic view of an aphaeresis system.

A preferred blood aphaeresis system 2 for use in and/or with the present invention is schematically illustrated in FIG. 1. System 2 preferably provides for a continuous blood component separation process. Generally, whole blood is withdrawn from a donor and is substantially continuously provided to a blood component separation device 6 where the blood is continuously separated into various component types and at least one of these blood component types is preferably continuously collected from the device 6. One or more of the separated blood components may then either be provided for collection and subsequent use by another through transfusion or may be uncollected and then returned to the donor. Therapeutic treatment and near immediate return of certain separated blood components is a viable, yet less common alternative use as well. It is also understood that for therapeutic treatment the blood may be separated into components with filtration using the principles of the instant invention and as described below at a patient's bedside for return to such patient.

In the blood aphaeresis system 2, blood is withdrawn from the donor and directed through a pre-connected bag and tubing set 8 which includes an extracorporeal tubing circuit 10 and, in one embodiment, a blood processing vessel 12 which together define a closed, sterile and disposable system. The set 8 is preferably disposable and is adapted to be mounted on and/or in the blood component separation device 6. The separation device 6 preferably includes a pump/valve/sensor assembly 14 for interfacing with the extracorporeal tubing circuit 10, and a channel assembly 16 for interfacing with the disposable blood processing vessel 12.

The channel assembly 16 may include a channel housing 18 that is rotatably interconnected with a rotatable centrifuge rotor assembly 20, which provides the centrifugal forces required to separate blood into its various blood component types by centrifugation. The blood processing vessel 12 may be fitted within the channel housing 18. When connected as described, blood can be flowed substantially continuously from the donor, through the extracorporeal tubing circuit 10, and into the rotating blood processing vessel 12. The blood within the blood processing vessel 12 may then be continuously separated into various blood component types and at least one of these blood component types (platelets, plasma, or red blood cells) is preferably continually removed from the blood processing vessel 12. Blood components which are not being retained for collection or for therapeutic treatment are preferably also removed from the blood processing vessel 12 and returned to the donor via the extracorporeal tubing circuit 10. Various alternative aphaeresis systems (not shown) may also make use of the present invention, including batch processing systems (non-continuous inflow of whole blood or non-continuous outflow of separated blood components) or smaller scale batch or continuous RBC/plasma separation systems, whether or even if no blood components may be returned to the donor.

Operation of the blood component separation device 6 is preferably controlled by one or more processors included therein, and may advantageously comprise a plurality of embedded computer processors to accommodate interface with ever-increasing PC user facilities (e.g., CD ROM, modem, audio, networking and other capabilities). In order to assist the operator of the aphaeresis system 2 with various aspects of its operation, the blood component separation device 6 preferably includes a graphical interface 22 with an interactive touch screen 24.

Further details concerning the operation of a preferred aphaeresis system, such as the Gambro Trima® System and the Trima® Accel™ System (available from the assignee of this application, Gambro BCT, Inc., Lakewood, Colo.) may be found in a plurality of publications, including, for example, WO99/11305 and U.S. Pat. Nos. 5,653,887; 5,676,644; 5,702,357; 5,720,716; 5,722,946; 5,738,644; 5,750,025; 5,795,317; 5,837,150; 5,919,154; 5,921,950; 5,941,842; and 6,129,656; among numerous others. The disclosures are incorporated herein. A plurality of other known aphaeresis systems may also be useful herewith, as for example, the Baxter CS3000®, Amicus®, Autopheresis-C®, and Alyx systems or the Haemonetics MCS® and MCS®+, or the Fresenius COM.TEC™ and AS-104™ or like systems.

Disposable Set: Extracorporeal Tubing Circuit

Figure 2:
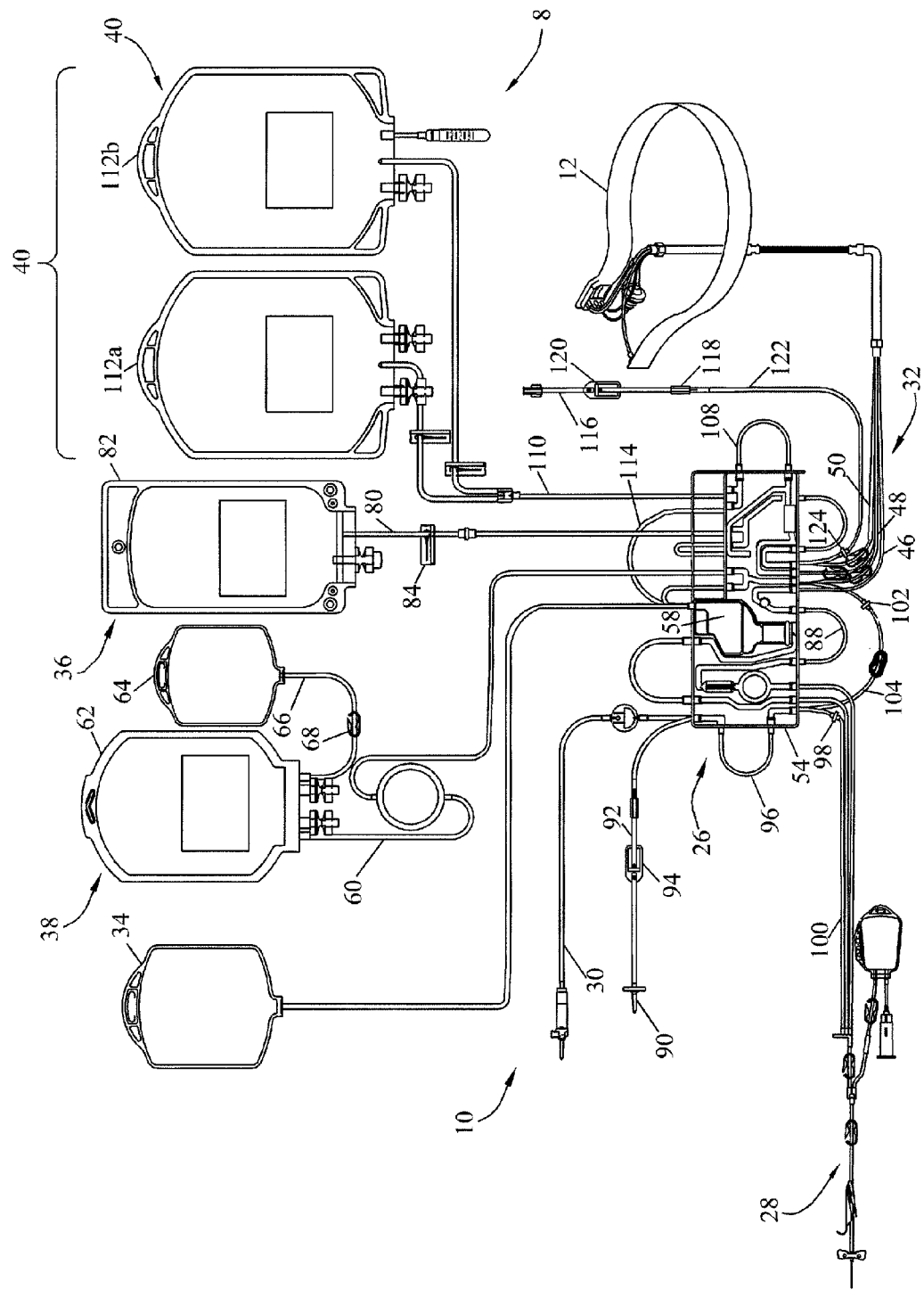
FIG. 2 illustrates a tubing and bag set including an extracorporeal tubing circuit, a cassette assembly, and collection bag assembly for use with the system of FIG. 1, pursuant to the present invention.
Figure 3:
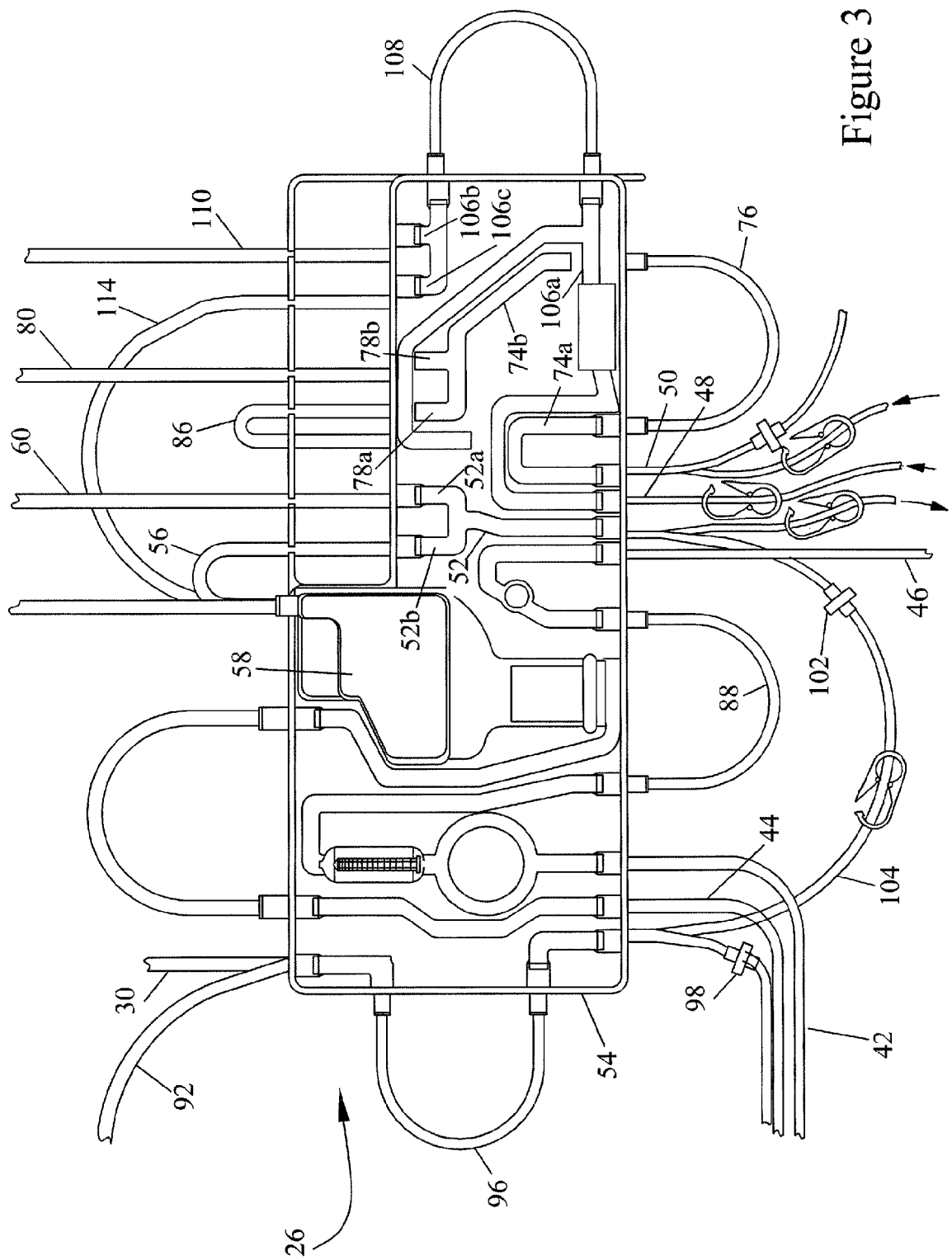
FIG. 3 illustrates a cassette assembly as shown in the set of FIG. 2.
Figure 4:
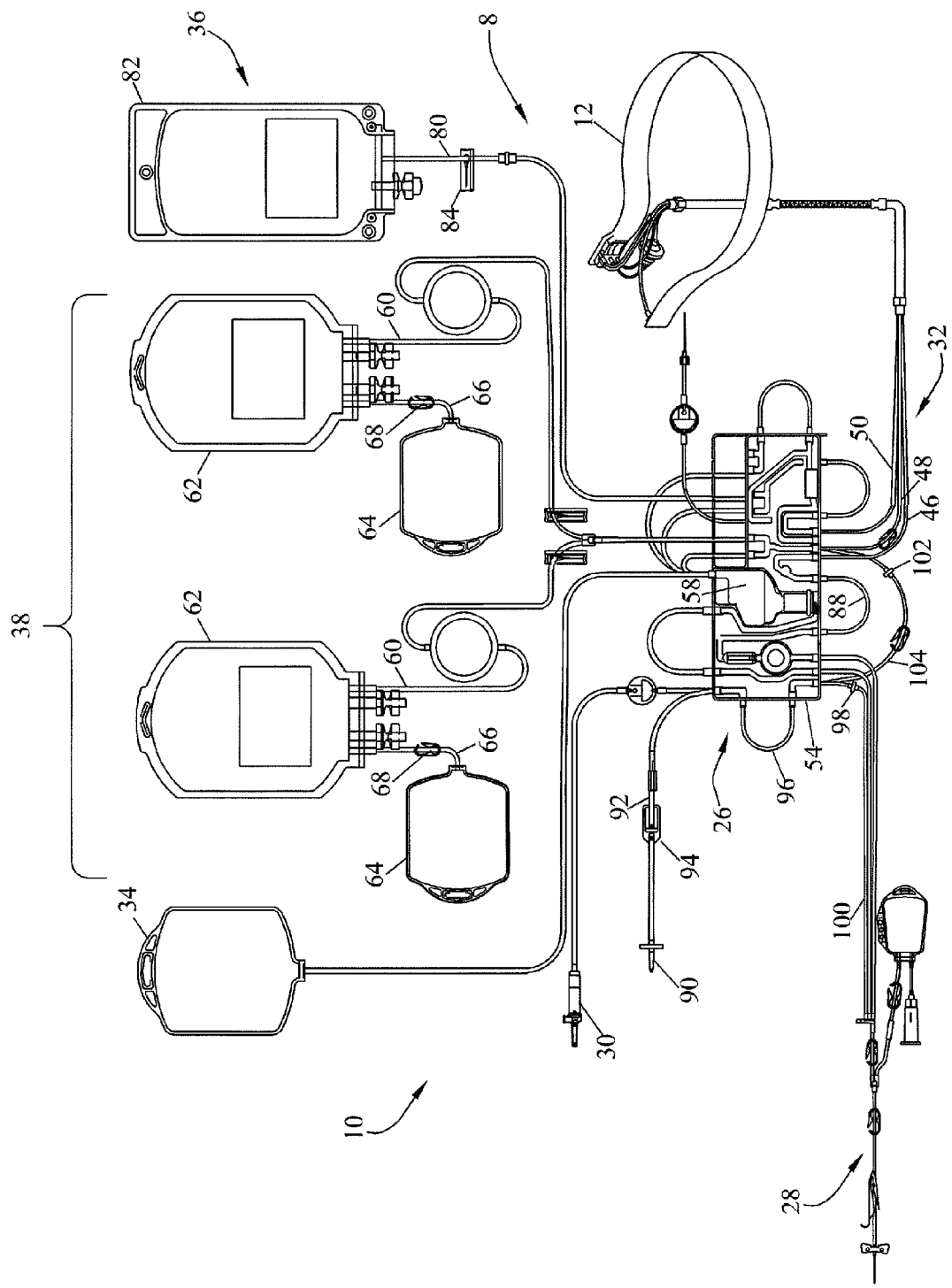
FIG. 4 illustrates an alternative tubing and collection bag assembly, also usable like the tubing and bag set shown in FIG. 2.

As illustrated in FIGS. 2, 3 and 4, the pre-connected extracorporeal tubing circuit 10 is shown which may include a cassette assembly 26 and a number of tubing/collection assemblies 28, 30, 32, 34, 36, 38 and 40 interconnected therewith. Preferably, a blood removal/return tubing assembly 28 provides a single needle interface between a donor and the remainder of the tubing circuit 10 (although a two-needle set-up may also be used, not shown). At least two lines 42, 44 are provided in assembly 28 (see FIG. 3) for removal of blood from and return of components to the donor. This embodiment includes a cassette assembly 26, which is interconnected between the tubing assembly 28, which connects the donor thereto, and blood inlet/blood component outlet tubing line sub-assembly 32, which provides the interface between cassette assembly 26 and blood processing vessel 12. Three lines 46, 48 and 50 are shown in FIGS. 2 and 3 for transport of blood and components to and from the processing vessel 12. An anticoagulant tubing assembly 30, a plasma collection tubing and bag assembly 36, a red blood cell collection assembly 38, a vent bag tubing line sub-assembly 34, and a platelet assembly 40 are also interconnected with cassette assembly 26 in this embodiment. As will be appreciated, the extracorporeal tubing circuit 10 and blood processing vessel 12 are preferably pre-interconnected to yield a closed, pre-sterilized disposable assembly for a single use.

Emanating from vessel 12 is an RBC outlet tubing line 48 of the blood inlet/blood component tubing assembly 32 which is interconnected with integral RBC passageway 52 of cassette 54 of cassette assembly 26 (see FIGS. 2 and 3). The integral RBC passageway 52 includes first and second spurs 52a and 52b, respectively. The first spur 52a is interconnected with RBC return tubing loop 56 to return separated RBCs to a donor. For such purpose, the RBC return tubing loop 52 is preferably interconnected to the top of a blood return reservoir 58 of the cassette assembly 26. The second spur 52b may, as preferred herein, be connected with an RBC collection tubing assembly 38 (see FIGS. 2, 3 and 4, for example) for collecting RBCs during use. RBC collection tubing and bag assembly 38 preferably includes RBC collector tubing line 60 which communicates with spur 52b, an RBC collection reservoir or bag 62, and an air removal bag 64. The air removal bag 64 is attached to the RBC collection bag 62 by a tubing line 66 which may have an optional clamp 68, (FIG. 4), attached thereto. The RBC collection tubing line and container sub-assembly 38 is preferably a pre-connected part of the disposable assembly 8.

In a portion of the cassette assembly 26, plasma tubing 50 of blood inlet/blood component tubing assembly 32 (see FIGS. 2 and 3) interconnects with a first integral plasma passageway 74a (see FIG. 3) of cassette assembly 26 (note, this is preferably a plasma collection sub-system; however, other components such as platelets could alternatively be collected here or with a similar arrangement). Cassette assembly 26 further includes a pump-engaging, plasma tubing loop 76 interconnecting the first integral plasma passageway 74a and a second integral plasma passageway 74b. The second integral plasma passageway 74b includes first and second spurs 78a and 78b. The first spur 78a is interconnected to the plasma collection tubing assembly 36 via tubing line 80. The plasma collection tubing assembly 36 maybe employed to collect plasma during use and includes plasma collector tubing 80 and plasma collection bag 82. A slide clamp 84 (see FIG. 2) may be provided on plasma collector tubing 80. The second spur 78b of the second integral plasma passageway 74b is interconnected to a plasma return tubing loop 86 to return plasma to donor/patient. For such purpose, the plasma return tubing loop 86 is interconnected through loops 108 and 114 to the top of the blood return reservoir 58 of the cassette assembly 26. One or more types of uncollected blood components, e.g., plasma and/or platelets, collectively referred to as return blood components, will cyclically accumulate in and be removed from reservoir 58 during use. Here also, valve/clamp access is made through cassette assembly 26 to maintain the plasma collector tubing 80 and plasma return tubing loop 86 in a predetermined spaced relationship for flow control therethrough.

Most portions of the tubing assemblies 28, 30, 32, 36, 34, 38, and 40 and cassette assembly 26 are preferably made from plastic components including, for example, polyvinyl chloride (PVC) tubing lines, that may permit visual observation and monitoring of blood/blood components during use. It should be noted that thin-walled PVC tubing may be employed for approved, sterile docking (i.e., the direct connection of two pieces of tubing line) for the RBC collector tubing lines 60, inter alia. All tubing lines are pre-connected before sterilization of the total disposable assembly to assure that maximum sterility of the system is maintained. A highly desirable advantage of pre-connection of all of the elements of the tubing circuit including the collection bag sub-assembly 38 involves the complete pre-assembly and then sterilization hereof after pre-assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 60, inter alia.

As mentioned, a cassette assembly 26 in the embodiment of FIG. 3, may be mounted upon and operatively interface with the pump/valve/sensor assembly 14 of a blood component separation device 6 during use. Further details of an aphaeresis system set-up including the loading and interaction of a disposable assembly 8 with a blood component separation device 6, may be found in the above-listed patents, inter alia, and are not exhaustively repeated here.

Operation of Extracorporeal Tubing Circuit and Blood Component Separation Device Priming and various other operations of the aphaeresis process are preferably carried out as set forth in the above-listed patents. During a blood removal, whole blood will be passed from a donor into tubing line 44 of blood removal/return tubing assembly 28 and is then transferred to blood component separation device 6. At device 6, the blood is flowed, preferably pumped via loop 88 (see FIG. 3), to the processing vessel 12 via the cassette assembly 26 and line 46 of the blood inlet/blood component tubing assembly 32 (FIGS. 2 and 3). Separation processing then occurs on a substantially continuous basis in vessel 12; i.e., blood flows therein, is separated and flows as separated components therefrom. After separation processing in vessel 12 (though separation is continuously occurring), uncollected blood components are transferred from the processing vessel 12 to and through cassette assembly 26, into and may then accumulate in reservoir 58 (FIGS. 2 and 3) of cassette 26 up to a predetermined level at which the blood component separation device 6, in a single needle operation, may (though in a continuous system, need not) pause the blood removal submode and initiate a blood return submode wherein these uncollected and/or treated components may be returned to the donor. As such, these accumulated components may be transferred into the blood return tubing line 44 of blood removal/return tubing assembly 28 and back into the donor. During the single needle blood return mode, when the accumulated return blood components in reservoir 58 are removed down to a predetermined level, blood component separation device 6 will then automatically end the blood return submode. This preferably will also automatically serve to reinitiate or continue the blood removal submode. The cycle between blood removal and blood return submodes will then continue until a predetermined amount of collected blood components have been harvested. In an alternative dual needle scheme, as is known in the art, blood may be continually removed from and blood components continually returned to a donor. The detailed mechanisms for such operations, including controlling the pumps, for example, are not shown or described in detail herein.

Also, certain components may be collected simultaneously or consecutively one after the other. In one example, platelets may be collected prior to collection of RBCs while plasma may be collected concurrently with either. In the primary example shown in FIGS. 1-3, three components are shown being collected, RBCs in the RBC sub-assembly 38 and plasma in assembly 36 and platelets in the other collection assembly 40. When a sufficient quantity of one or the other is collected, further separated portions of such a component are returned to the donor with any other uncollected components, until a sufficient quantity of all components are collected. One or two selected components may be collected with all other components being returned to the donor.

With specific reference to FIGS. 2 and 3, in normal operation, whole blood will pass from the donor through the needle and blood removal tubing assembly 28, cassette assembly 26 and blood inlet tubing line 46 to processing vessel 12. The whole blood will then be separated in vessel 12. Also, a platelet stream or a plasma stream may be separated herein and be either collected in a collector assembly 40 or 36, or diverted to reservoir 58 for ultimate return to the donor. Separated plasma may be flowed through cassette 26 via loop 76 and line 86 for collection in the container 82 for plasma or diverted to reservoir 58. Separated platelets may be flowed through cassette 26 via loop 108 and line 110 for collection in the containers 112a, 112b or diverted to reservoir 58 through loop 114. Further, red blood cells (including potentially some white blood cells) may be separated in and passed, preferably pushed from vessel 12 through RBC outlet tubing line 64, through cassette assembly 26 and, in return mode, into reservoir 58. In a preferred alternative, during an RBC collection procedure separated RBCs will be delivered to RBC collector tubing and bag assembly 38 through tubing line 60 for collection.

Aphaeresis Protocol

One preferred protocol, which may be followed for performing an aphaeresis procedure relative to a donor utilizing the described system 2, will now be summarized. Initially, an operator loads the disposable plastic assembly 8 in and/or onto the blood component separation device 6. According hereto, the operator hangs the various bags on hooks on the blood component separation device 6. If one is used, the operator then also loads the cassette assembly 26 on the device 6 and/or the blood processing vessel 12 within the channel housing 18 as mounted on the centrifuge rotor assembly 20 in the machine 6.

With the extracorporeal tubing circuit 10 and the blood processing vessel 12 loaded in the described manner, the donor may then be fluidly interconnected with the extracorporeal tubing circuit 10 by inserting an access needle of the needle/tubing assembly 28 into the donor. In addition, the anticoagulant tubing assembly 30 (see FIG. 2) is primed and the blood removal/return tubing assembly 28 is primed preferably with blood from the donor. The blood processing vessel 12 is also primed for the aphaeresis procedure. In one embodiment, a blood prime may be used in that blood will be the first liquid introduced into the blood processing vessel 12. During the priming procedure, as well as throughout the remainder of the aphaeresis procedure, blood maybe flowed into the vessel 12, blood components are separated from each other and one or more components is removed from the blood processing vessel 12.

The preferred blood aphaeresis system 2 provides for contemporaneous separation of a plurality of blood components during blood processing, including the separation of red blood cells (RBCs) and plasma, but optionally may provide for the separation and collection of platelets. In turn, such separated blood components may be selectively collected in corresponding storage reservoirs or immediately or after a minor delay returned to the donor during respective blood return submodes (or substantially constantly in a two-needle setup). In one approach where more than one blood component is to be collected, such as both plasma (and/or platelets) and RBCs, blood aphaeresis system 2 may be used to collect plasma (and/or if desired separated platelets), during a time period(s) separate from the collection of red blood cells. These components may also be collected simultaneously.

To initiate the RBC collection phase, blood component separation device 6 provides an appropriate control signal to the RBC divert valve assembly (not shown) so as to direct the outflow of the separated RBCs removed from blood processing vessel 12 via line 48 into the RBC collection system 38 through tubing line 60 into collection container 62. The separated RBCs are preferably not pumped out of vessel 12 for collection, but instead are flowed out vessel 12 and through extracorporeal tubing circuit 10 by the pressure of the blood inlet flow to vessel 12. The inlet blood is pumped into vessel 12 via loop 88 of cassette 26. Trauma to the collected RBCs would thereby be minimized.

Following the separation and collection of the desired quantity of red blood cells, blood separation device 6 may then provide a control signal to the RBC divert assembly so as to divert any further RBC flow back to the donor via loop 56, reservoir 58 and return line 44. Additionally, if further blood processing is not desired, rinse back procedures may be completed. According to the present invention, a storage solution will be added to the red blood cell reservoir or bag 62. Preferably, one or more storage solution bag(s) are connected to the circuit 10 through a spike 90. Such storage solutions or additive solutions may advantageously facilitate storage of the RBCs for up to about forty-two days at a temperature of about 1-6 degrees C. In this regard, acceptable storage solutions include a storage solution generically referred to in the United States as Additive Solution 3 (AS-3), available from Medsep Corp. located in Covina, Calif.; and/or a storage solution generically referred to in Europe as SAG-M, available from MacoPharma located in Tourcoing, France.

The storage additive solution may be and preferably is contained in a discrete storage solution bag (not shown) that can be pre-connected, or is separate and may be later connected to the tubing circuit 10 via line 92, preferably through spike connection 90. By way of example, one such sterile connecting device to interconnect a tubing line 92 to such a storage solution container is that offered under the trade name "TSCD" or "SCD™ 312" by Terumo Medical Corporation located in Somerset, N.J. The use of such a sterile barrier filter/spike assembly 90 facilitates the maintenance of a closed system, thereby effectively avoiding bacterial contamination.

In order to ensure the maintenance of RBC quality, the collection RBC bag 62, the storage solution, and the anticoagulant used during blood processing should be compatible. For example, the collection bag 62 may be a standard PVC DEHP reservoir (i.e. polyvinyl chloride-diethylhexylphthallate) such as those offered by the Medsep Corporation. Alternatively, other PVC reservoirs may be employed. Such a reservoir may utilize a plasticizer offered under the trade name "CITRIFLEX-B6" by Moreflex located in Commerce, Calif. Further, the anticoagulant utilized in connection with the above-described red blood cell collection procedures may be an acid citrate dextrose-formula A (ACD-A).

Any air from bag 62, or air caught between the incoming RBCs and bag 62 is ultimately removed to air removal bag 64 through tubing line connection 66. The air is evacuated to air removal bag 64 prior to the flow of the incoming RBCs or is evacuated by the flow of the incoming RBCs. Air can also be vented prior to the separation process by initially running the return pump, (not shown) of the aphaeresis system. Removal of air may also be achieved by other known (though less desirable here) methods, including, for example, hydrophobic vents and/or by-pass lines.

After completion of the collection, storage solution is added to the RBCs. After a storage solution bag (not shown) is connected (by pre-connection or by spike or by sterile welding), clamp 94 is opened to allow the introduction of the storage solution into tubing line 92. A first check valve 98 is closed in a feed line 100 between the anti-coagulant assembly 30 and the donor access 28. A second check valve 102 is opened in a crossover line 104, thus coupling the RBC storage solution assembly to the RBC line 48 from the separation channel 12. Storage solution can now be pumped through line 92, loop 96, crossover line 102 and spur 52a into the reservoir 58. Reservoir 58 is coupled to level and photo sensors, heretofore used to detect presence and quantity of separated RBC blood component. Now, as storage solution is pumped into the reservoir 58, the presence and quantity of the storage solution in the reservoir can be detected by the separation device 6 through the same sensors. After detecting a quantity of storage solution sufficient to indicate that the RBC blood component has been washed from the system, storage solution flow is diverted from the reservoir 58 into spur 52b, which is connected to line 60 and RBC storage bag 62. A metered quantity of storage solution can then be delivered to the bag 62 by controlled operation of a peristaltic pump acting on loop 96.

Upon completion of chasing with additive solution, the collection bag 62 may be separated from the rest of the set 8. The separation may be made by a clamp or by RF sealing the tubing line 60 and then separating in accordance with U.S. Pat. Nos. 5,345,070 and 5,520,218, inter alia, along the RF-sealed portion of the tubing line. Other well known methods can also be used to close the tubing line and then also separate the RBC collection system 38 from the remainder of the disposable assembly 8.

In the bag and tubing assembly 10 of FIG. 2, platelets may also be collected in platelet bag assembly 40. During blood component separation, platelets or plasma flow out of the separation channel 12 through platelet and plasma line 50 into spur 74a and loop 76. Loop 76 engages a peristaltic pump on the blood separation apparatus 6. Plasma flows through a valve (not shown) into spur 74b and either into spur 78a, which is connected to line 80 and plasma bag 82, or into spur 78b, which is connected to crossover line 104 and reservoir 58 for return to the donor. Under appropriate conditions in the separation channel 12, platelets also flow through line 50 into spur 74a and loop 76, but are then diverted by a valve into spur 106a and loop 108. Loop 108 also engages a peristaltic pump on the blood separation apparatus 6. Platelets flow through a valve either into spur 106b, which is connected to line 110 and platelet bags 112a and 112b of the platelet bag assembly 40, or into spur 106c, which is connected to crossover line 114 and reservoir 58 for return to the donor.

After completion of the collection, red blood cells must be cleansed from the cassette by application of positive and negative pressure, as described below in connection with vacuum purge step 196. Storage solution is added to the platelets. After a storage solution bag (not shown) is connected to a platelet storage solution assembly 116 (by pre-connection or by spike or by sterile welding), a frangible valve 118 or clamp 120 is opened to allow the introduction of the storage solution into a tubing line 122. A third check valve 124 is opened in line 122, thus coupling the platelet storage solution assembly to the platelet and plasma line 50 from the separation channel 12. Storage solution can now be pumped through line 50, loop 76, spur 106a, loop 108, spur 106c, crossover line 114 into the reservoir 58. As explained above, reservoir 58 is coupled to level and photo sensors. Storage solution is pumped into the reservoir 58 using the vacuum purge procedure 196, and the presence and quantity of the storage solution in the reservoir is detected by the separation device 6 through the same sensors. After detecting a quantity of storage solution sufficient to indicate that the platelet blood component has been washed from the system, storage solution flow is diverted from the reservoir 58 into spur 106b, which is connected to line 110 and platelet storage bags 112a and 112b. A metered quantity of storage solution can then be delivered to the bags by controlled operation of peristaltic pumps acting on loops 76 and 108.

Figure 5:
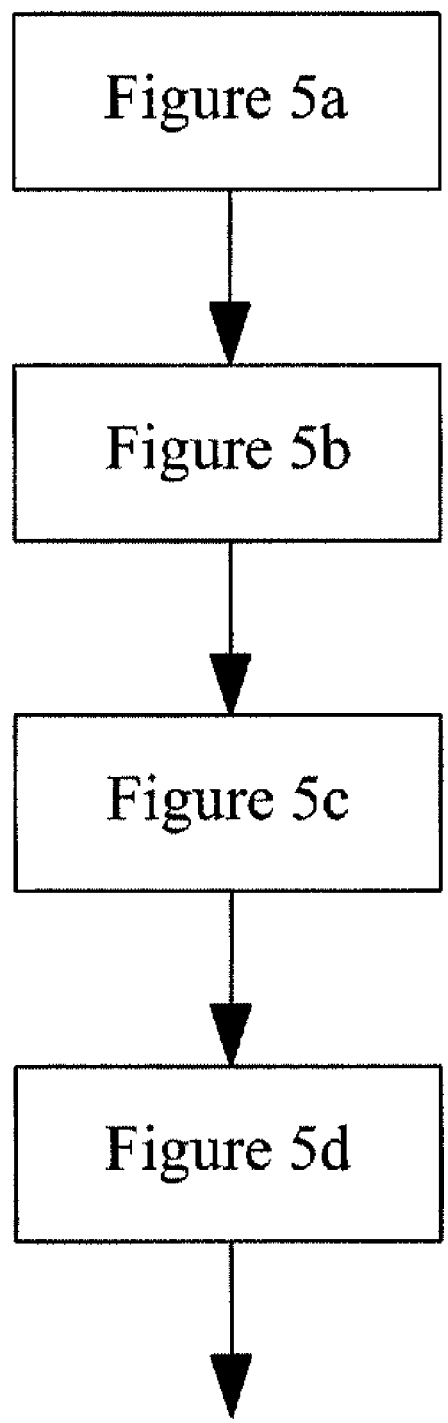
FIG. 5 is a software diagram for control of an aphaeresis system for providing a metered amount of storage solution according to the present invention.
Figure 5A:
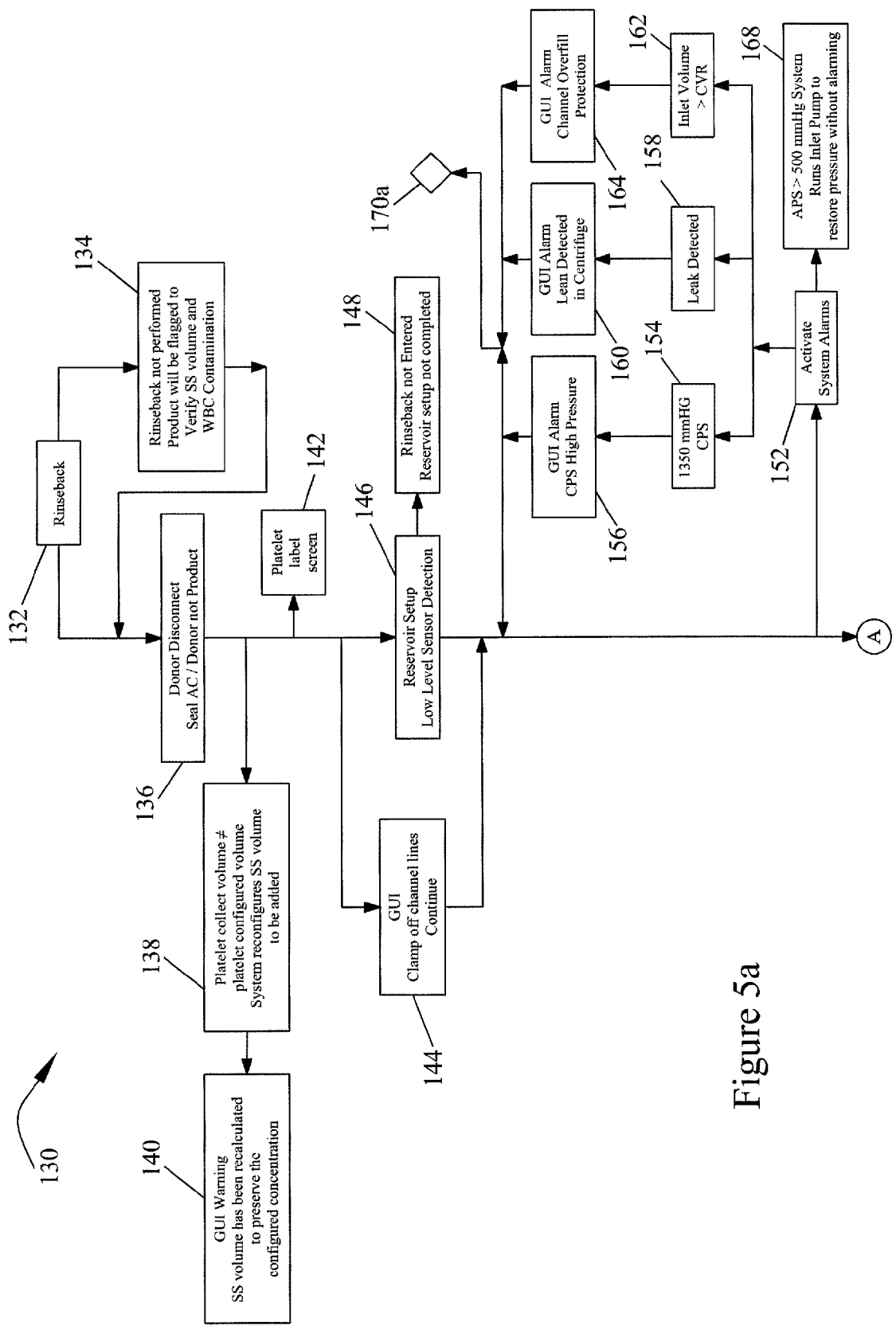
Figure 5B:
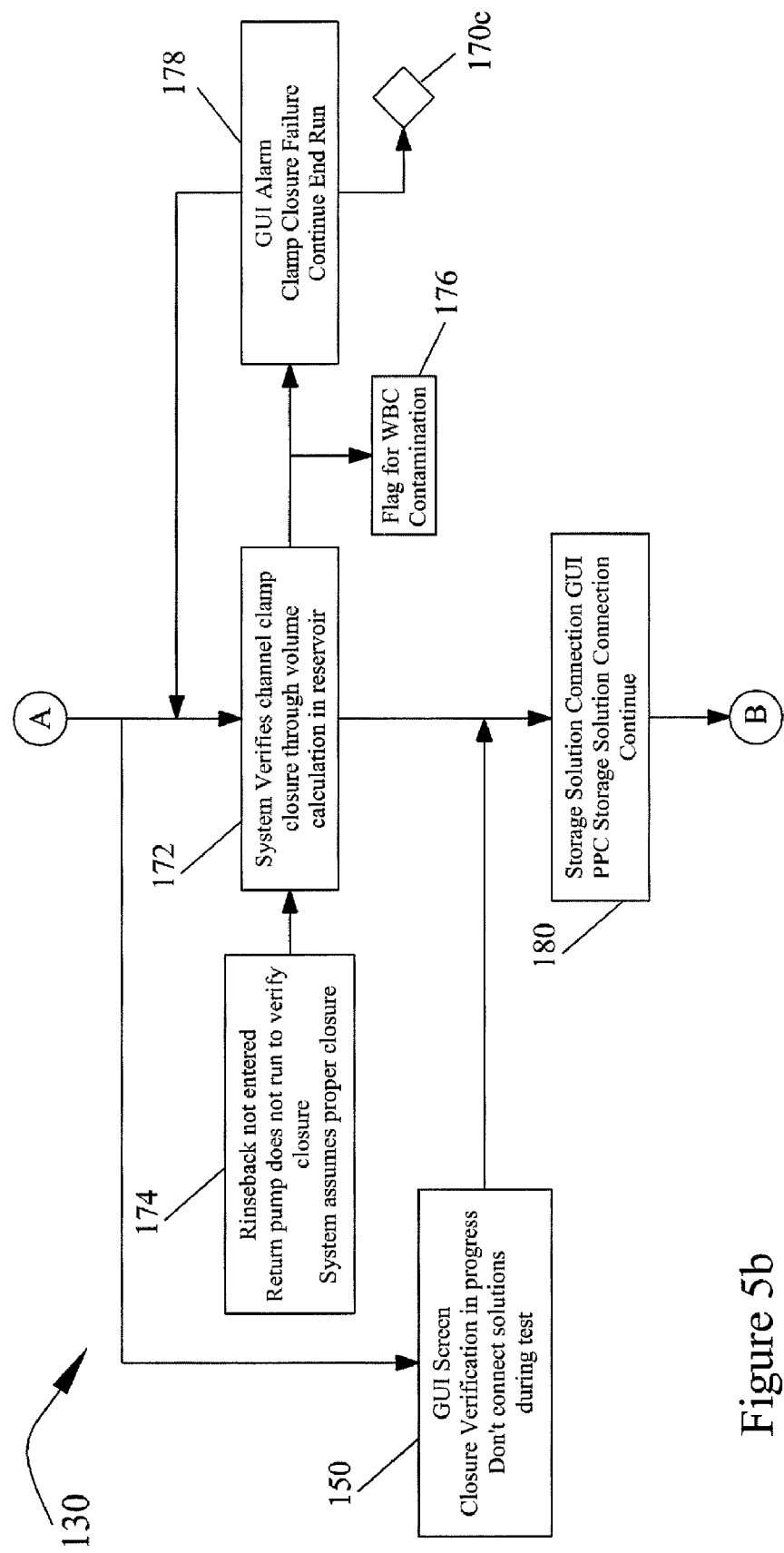
Figure 5C:
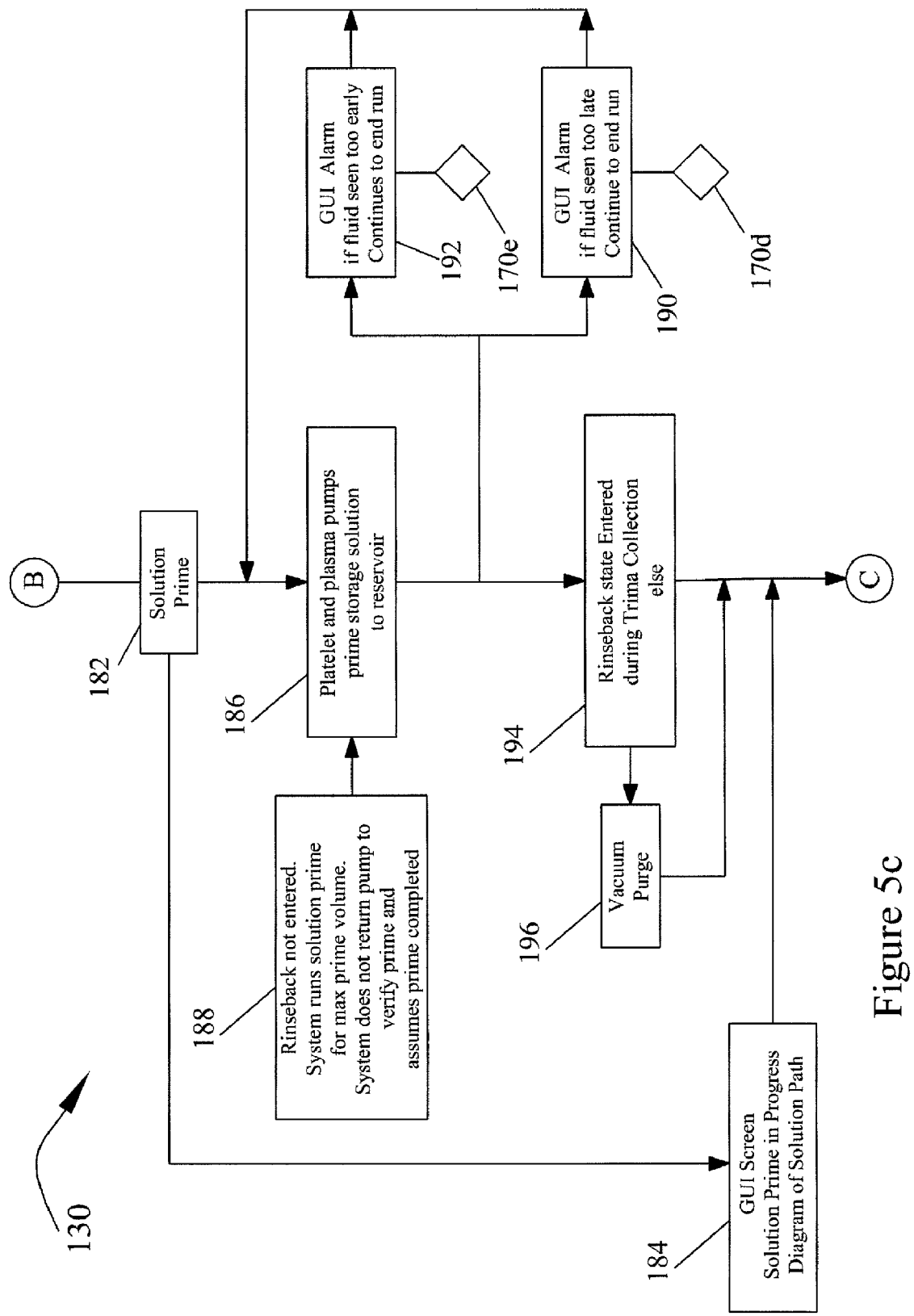
Figure 5D:
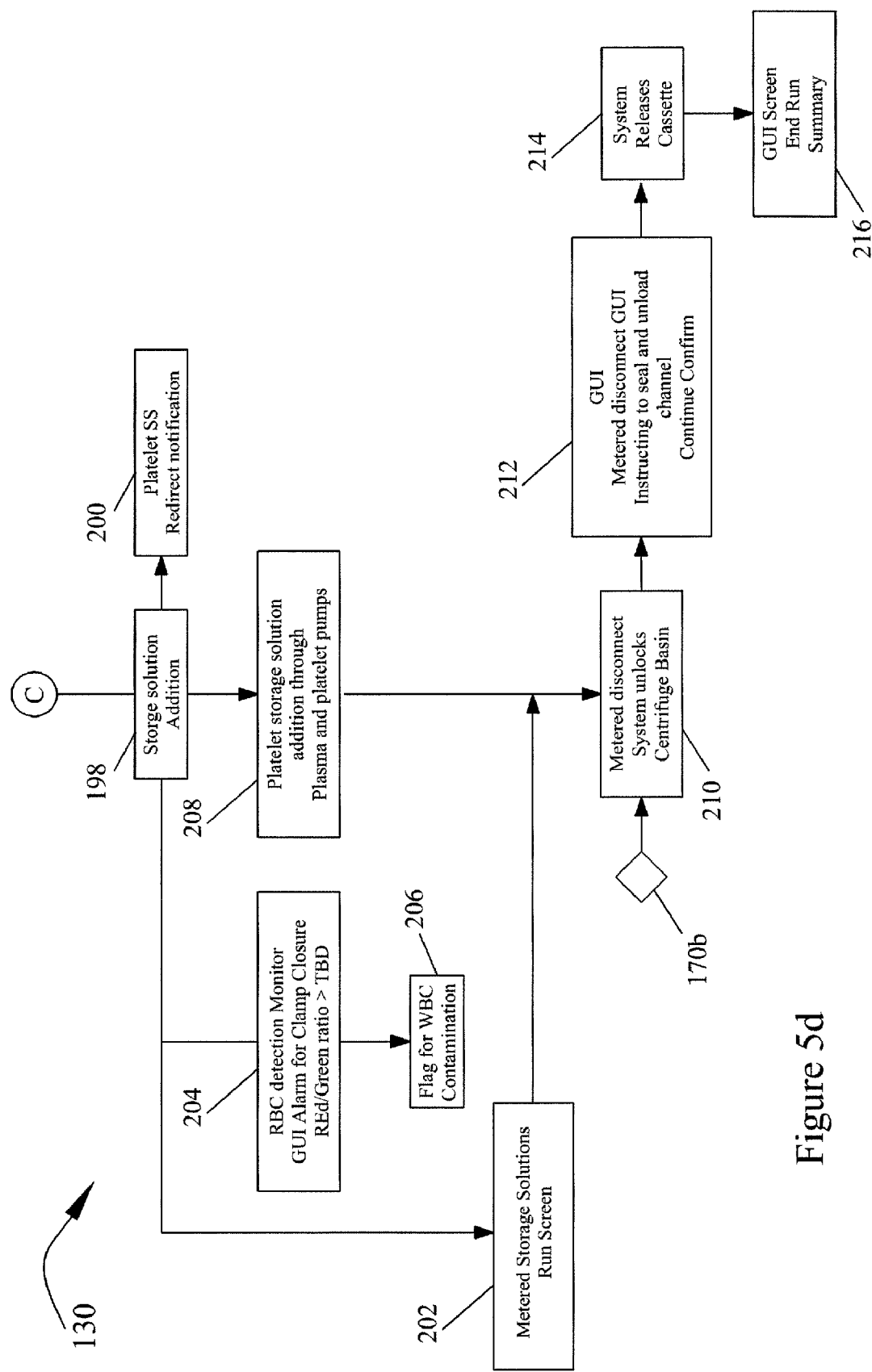

FIG. 5 shows a control program 130 whereby the blood separation device 6 controls the delivery of metered storage solution to collected blood products. Programming for standard collection of blood products such as red blood cells, platelets, or plasma is well known and is not illustrated here. The final step in such known processes is generally a rinseback step 132, which comprises washing uncollected blood components out of the separation channel and the tubing and returning these components to the donor. The rinseback step 132 is a suitable starting condition for the metered storage solution program. If rinseback is not performed successfully, the product is flagged 134 to manually verify the storage solution volume and to check for white blood cell contamination. After either rinseback 132 or flagging 134, the apparatus is disconnected 136 from the donor and the anti-coagulant 30 and donor lines 28 are sealed. The device 6 determines 138 whether the volume of collected platelets is different from the pre-selected or configured volume, and, if different, re-calculates a volume of storage solution to be added to the collected platelets. The device 6 displays 140 a message on the graphical user interface (GUI) 22, alerting the operator that the storage solution volume has been re-calculated. A platelet label screen is shown 142 so that an appropriate label may be produced. The device prompts 144 the operator to clamp off channel lines. At the same time, the reservoir 58 is prepared 146 to detect storage solution by lowering the fluid level to a low level sensor detector. The reservoir preparation is not completed 148 if rinseback 132 was not entered as part of the normal system control.

The system continues to prepare to provide monitored storage solution by, first, notifying 150 the operator through the GUI 22 that closure verification is in progress. Second, system alarms are activated 152 to detect adverse operating conditions. If a pressure above 1350 mmHg is detected 154, a high pressure alarm is given 156. If system pressure is greater than 500 mmHG, but less than the alarm pressure, the system runs 168 the inlet pump to restore pressure, without giving an alarm. A leak, another adverse operating condition, maybe sensed 158 in the centrifuge 18, and a leak alarm may be displayed 160. Finally, excess inlet volume may be detected 162, in which case, channel overfill protection would be invoked 164. If any of the alarm conditions are detected and not cleared, further automatic delivery of metered storage solution is terminated by branching 170a to a program termination 170b. Otherwise, preparation to provide storage solution continues. The system 6 verifies 172 channel clamp closure by calculating volume in the reservoir 58. However, if rinseback 132 was not performed, the return pump does not run to verify closure; rather, the system assumes 174 proper closure and continues processing. If channel clamp closure is not verified, a flag indicating possible white blood cell contamination may be set 176, and a clamp closure alarm may be displayed 178. If this alarm is not cleared, the program branches 170c to the program termination 170b.

When preparation is complete, the system prompts 180 for the operator to connect storage solution bags to the platelet storage solution assembly 116 or the RBC storage solution assembly 90 or both. After operator confirmation, the system begins to prime 182 with storage solution. A screen on the GUI notifies 184 the operator that solution priming is in progress. At the same time, the platelet and plasma pumps prime 186 storage solution into the reservoir 58, where sensors detect the character (clear fluid) and volume (upper level sensor) of the solution pumped to the reservoir. Such sensors are known from other patents mentioned above, and need not be further described here. If rinseback 132 was not performed, the system runs 188 the pumps to deliver a maximum volume of solution for priming. The system does not run the return pump to verify priming, and assumes that priming is completed with the delivery of the selected maximum volume. During priming, an alarm maybe given 190 if solution appears to be arriving at the reservoir after a predetermined time. Late arrival may indicate an improperly fastened clamp, a leak, or some other failure. If the operator is unable to determine the cause and clear the alarm, the program branches 170*d* to the program termination 170*b*. Similarly, if solution is detected in the reservoir too early 192, clamps or valves may not be set properly and solution may not be reaching all necessary areas. Again, if the operator is unable to determine the cause and clear the alarm, the program branches 170*e* to the program termination 170*b*.

If rinseback 132 was performed 194 and if storage solution is to be added to collected platelets or plasma, the system performs a vacuum purge 196 which removes unwanted red blood cells and white blood cells from the passageways of the cassette 26. It is important to cleanse the passageways of the cassette 26 to avoid contaminating the collected platelets or plasma with certain blood components. At the same time, it is desirable to use as small an amount of storage solution for this cleansing process as possible. With platelet storage solution available through line 122, the blood processing apparatus 6 controls pumps engaging loops 76 and 108. The pump on loop 108 is initially stopped while the pump engaging loop 76 pumps platelet storage solution (for example, about 1.4 mL) thereby creating a positive pressure within the channels of the cassette 26. Next, the pump engaging loop 108 is activated, while the pump engaging loop 76 operates at a reduced rate, substantially slower than the loop 108 pump. This produces a partial vacuum or negative pressure in the channels of the cassette 26, while still permitting fluid flow. The steps of pressurizing to a positive pressure and of flowing fluid at a negative pressure are repeated, for example, four times, whereby about 6 mL of storage solution is used to cleanse the cassette. Cyclic pressurizing to a positive pressure and flowing at a negative pressure causes blood particles, such as red blood cells and white blood cells, to be drawn out of side channels in the cassette 26, that is, channels which are not directly in the flow path between the platelet storage solution and the platelet collect bags 112*a*, 112*b*. The 6 mL of storage solution used for cleansing and any blood particles drawn into the flow path by cyclic positive and negative pressure flow through loop 114 into the reservoir 58. This process of vacuum purging 196 primes the system for the delivery of storage solution.

Priming assures that storage solution is available in the system and can be pumped into the platelet or RBC storage bags in a metered fashion without contaminating blood components, as controlled by the peristaltic pumps, thus assuring a correct mixture of blood component and storage solution with less operator intervention. With priming complete the system switches the orientation of valves to direct solution into selected product bags and begins to add 198 storage solution. During this process, if a error is detected, the operator can be notified 200 to resume manual addition of storage solution. During metered delivery of storage solution, the GUI 22 displays 202 a metered storage solution run screen, notifying the operator of the status of the procedure. Sensors, known from the above-mentioned patents, in the device 6 monitor 204 for the presence of RBC (red blood cells), particularly if storage solution is being delivered to the platelet bags 112*a*, 112*b*. If unwanted blood components are detected, the product may be flagged 206 for possible white blood cell contamination. Operation of appropriate pumps delivers 208 a metered amount of storage solution, based on counted rotations of the peristaltic pumps, to the platelet bags 112*a*, 112*b*, the red blood cell bag 62, or both.

When the desired amount of storage solution has been delivered, the system performs a program termination by unlocking 210 the centrifuge basin. The system displays 212 instructions for the operator to unload the separation chamber 12 from the channel housing 18. The system also raises 214 the cassette assembly 26, allowing the cassette assembly to be removed from the device 6, and displays 216 an end of run screen.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A blood processing apparatus comprising
    a separation chamber adapted to be mounted on a rotor of said blood processing apparatus;
    a tubing set coupled to said separation chamber for conducting blood, blood components, and fluids to and from said separation chamber, said tubing set including at least one inlet line in fluid communication with said separation chamber and at least one outlet line in fluid communication with said separation chamber;
    an anti-coagulant line having a pump-engaging loop, said anti-coagulant line being in fluid communication with said inlet line;
    a reservoir in fluid communication with said outlet line, said reservoir having means for detecting a pre-determined quantity of fluid in said reservoir;
    a component collection bag in fluid communication with said reservoir;
    a storage solution line in fluid communication with said anti-coagulant line at a junction above said pump-engaging loop with respect to fluid flow, and
    a crossover line in fluid communication with said storage solution line below said pump-engaging loop with respect to fluid flow, said crossover line coupling said storage solution line to said reservoir, and
    means for selectively permitting fluid flow through said crossover line,
    whereby a predetermined quantity of storage solution may be delivered to said component collection bag through said reservoir.

2. The blood processing apparatus of claim 1 further comprising
    at least a first peristaltic pump;
    means for controlling said pump to conduct a predetermined quantity of storage solution through said crossover line into said reservoir.

3. The blood processing apparatus of claim 1 further comprising
    a second storage solution line in fluid communication with said outflow line immediately adjacent said separation chamber; and
    means for purging blood components in at least part of said tubing set into said reservoir prior to conducting said predetermined quantity of storage solution into said component collection bag.

4. The blood processing apparatus of claim 3 wherein said means for purging blood components comprises an apparatus for initially applying a positive pressure to fluid in at least a portion of said tubing set and for next applying a negative pressure to said fluid in said at least a portion of said tubing set while permitting fluid flow in said portion of said tubing set.

5. The blood processing apparatus of claim 4 further comprising
   a second peristaltic pump;
   a third peristaltic pump;
   a second segment of said outlet line configured to engage said third pump downstream from said second pump, said second segment being adjacent a connection adapted for communication with a blood component collection bag; and wherein said apparatus for applying pressure comprises
   a controller in communication with said second and third pumps, said controller activating at least said second pump to create said positive pressure between said second and third pumps and activating at least said third pump to create said negative pressure between said second and third pumps.

6. The blood processing apparatus of claim 5 wherein said controller further initially stops said third pump to create said positive pressure and next activates said third pump and activates said second pump at a rate less than said third pump to create said negative pressure.

7. The blood processing apparatus of claim 6 wherein said controller activates said second and third pumps to produce a series of positive pressures and negative pressures in said tubing set.

8. A disposable blood processing set for a centrifugal blood processing apparatus, said blood processing set comprising
   a separation chamber adapted to be mounted on a rotor of said centrifugal blood processing apparatus;
   a tubing set coupled to said separation chamber for conducting blood, blood components, and fluids to and from said separation chamber, said tubing set including at least one inlet line in fluid communication with said separation chamber and at least one outlet line in fluid communication with said separation chamber;
   an anti-coagulant line having a pump-engaging loop, said anti-coagulant line being in fluid communication with said inlet line;
   a reservoir in fluid communication with said outlet line, said reservoir having means for detecting a pre-determined quantity of fluid in said reservoir;
   a component collection bag in fluid communication with said reservoir;
   a storage solution line in fluid communication with said anti-coagulant line at a junction above said pump-engaging loop with respect to fluid flow, and
   a crossover line in fluid communication with said storage solution line below said pump-engaging loop with respect to fluid flow, said crossover line coupling said storage solution line to said reservoir, and
   means for selectively permitting fluid flow through said crossover line,
   whereby a predetermined quantity of storage solution may be delivered to said component collection bag through said reservoir.

* * * * *